(12) United States Patent
Cauceglia et al.

(10) Patent No.: US 10,883,925 B2
(45) Date of Patent: Jan. 5, 2021

(54) SPECTROPHOTOMETER FOR USE IN EXPLOSIVE ATMOSPHERES

(71) Applicant: HF Scientific, Inc., Fort Myers, FL (US)

(72) Inventors: Dorian Cauceglia, Cape Coral, FL (US); Thomas R. Whiteside, North Fort Myers, FL (US); Michael J. Goodman, Fort Myers, FL (US); Charlie G. Pasquariello, Fort Myers, FL (US); Nicholas J. Pusateri, Cape Coral, FL (US); Thomas F. Grassi, Fort Myers, FL (US)

(73) Assignee: HF Scientific, Inc., Fort Myers, FL (US)

( * ) Notice: Subject to any disclaimer, the term of this patent is extended or adjusted under 35 U.S.C. 154(b) by 125 days.

(21) Appl. No.: 16/139,555

(22) Filed: Sep. 24, 2018

(65) Prior Publication Data

US 2020/0096440 A1    Mar. 26, 2020

(51) Int. Cl.
*G01J 3/42* (2006.01)
*G01N 21/25* (2006.01)
(Continued)

(52) U.S. Cl.
CPC .............. *G01N 21/251* (2013.01); *G01J 3/50* (2013.01); *G01N 21/255* (2013.01);
(Continued)

(58) Field of Classification Search
CPC ........ G01J 3/02; G01J 3/42; G01J 3/28; G01J 2003/2866; G01N 21/274
(Continued)

(56) References Cited

U.S. PATENT DOCUMENTS 5,067,616 A    11/1991 Plester et al.
5,083,865 A    1/1992 Kinney et al.
(Continued)

FOREIGN PATENT DOCUMENTS

WO    WO-2009094761 A1    8/2009

OTHER PUBLICATIONS

ISA/US, International Search Report & Written Opinion for Corresponding International Application No. PCT/US19/51900, dated Dec. 18, 2019 (16 pgs).
(Continued)

*Primary Examiner* — Md M Rahman
(74) *Attorney, Agent, or Firm* — Harris Beach PLLC

(57) ABSTRACT

A spectrophotometer includes an electronics compartment having disposed within, at least one light source, and at least one optical detector. A testing compartment has disposed within, an optical block having at least one fluid connection port, and a first light pipe optically coupled between the at least one light source and the optical block. A second light pipe is optically coupled between the optical block and the at least one optical detector. The testing compartment is adapted to perform spectrophotometry of a fluid sample disposed within a sample container in the optical block, and the electronics compartment is electrically isolated from the testing compartment. A spectrophotometer for use in an explosive atmosphere and a method of measuring a presence or concentration of an organic or inorganic compound in a fluid in an explosive atmosphere are also described.

23 Claims, 7 Drawing Sheets

(51) Int. Cl.
*G01J 3/50* (2006.01)
*G01N 21/27* (2006.01)
*G01N 33/18* (2006.01)

(52) U.S. Cl.
CPC ....... *G01N 21/274* (2013.01); *G01N 33/1886* (2013.01); *G01N 2201/0236* (2013.01)

(58) Field of Classification Search
USPC ........................................................ 356/319
See application file for complete search history.

(56) References Cited

U.S. PATENT DOCUMENTS

| | | | |
|---|---|---|---|
| 5,880,850 | A | 3/1999 | McAndrew et al. |
| 7,794,660 | B2 | 9/2010 | Connelly et al. |
| 8,119,068 | B2 | 2/2012 | Connelly et al. |
| 2002/0187558 | A1 | 12/2002 | Bodkin et al. |
| 2004/0155516 | A1* | 8/2004 | Colussi ................ B60C 23/003 301/5.24 |
| 2011/0173721 | A1* | 7/2011 | Albino .................. A24B 13/00 800/286 |
| 2012/0103823 | A1 | 5/2012 | Dweik et al. |
| 2014/0212986 | A1 | 7/2014 | Angelescu et al. |
| 2017/0137877 | A1 | 5/2017 | McCaffrey et al. |
| 2017/0254752 | A1 | 9/2017 | Palassis et al. |
| 2019/0136393 | A1* | 5/2019 | Dopp ........................ C25B 9/16 |

OTHER PUBLICATIONS

HF Scientific, Inc., CLX-XT Extended Reagent Life OnLine Chlorine and TRO Minotor, Jun. 24, 2014 (1 pg).
HF Scientific, Inc., Ballast Water Online TRO and Chlorine Monitoring Solutions, PG-HF-BallastWater 1535, MF10403 (12 pgs).
Photonics, Fiber Optic CCD Array UV-Vis Spectrophotometer, undated, (4 pgs).
Intertek, EC-Type Examination Certificate, Dec. 23, 2011 (3 pgs).
Hach, 1735 TRO Analyzer, Hazardous Location Installation Manual, Jul. 2012, Edition 1 (46 pgs).
Hach, 1735 TRO, User Manual, Nov. 2012, Edition 2 (104 pgs).
Hach, 1735 TRO, Total Residual Oxidant Analyzer, 2012 (2 pgs).
PC 950 Probe Colorimeter User Manual, undated, (4 pgs).

* cited by examiner

SPECTROPHOTOMETER FOR USE IN EXPLOSIVE ATMOSPHERES

FIELD OF THE APPLICATION

The application relates to spectrophotometers, and particularly to spectrophotometers for use in explosive atmospheres.

BACKGROUND

A spectrophotometer measures light transmission through a sample fluid at a particular wavelength of light. A reagent added to the fluid changes the color of the fluid, thus changing the transmission of light through the fluid based on the presence of a material to be detected. A colorimeter is a type of spectrophotometer operating a visible wavelength.

SUMMARY

According to one aspect, a spectrophotometer includes an electronics compartment having disposed within, at least one light source, and at least one optical detector. A testing compartment has disposed within, an optical block having at least one fluid connection port, and a first light pipe optically coupled between the at least one light source and the optical block. A second light pipe is optically coupled between the optical block and the at least one optical detector. The testing compartment is adapted to perform spectrophotometry of a fluid sample disposed within a sample container in the optical block, and the electronics compartment is electrically isolated from the testing compartment.

In one embodiment, at least one of the first light pipe or the second light pipe includes an acrylic plastic.

In another embodiment, at least one of the first light pipe or the second light pipe includes a PTC connector to mechanically coupled the at least one of the first light pipe or the second light pipe to the optical block.

In yet another embodiment, the spectrophotometer further includes another light pipe to illuminate the fluid sample in the optical block with a back light for visual observation of a presence and color of the fluid sample.

In yet another embodiment, the spectrophotometer further includes another light pipe to illuminate the fluid sample in the optical block with a calibration light to automatically determine a presence of fluid in the optical block.

In yet another embodiment, the at least one light source includes a visible light.

In yet another embodiment, the spectrophotometer includes a colorimeter, and wherein the at least one optical detector measures an amplitude of light at a particular color.

In yet another embodiment, the at least one optical detector measures an amplitude of light at a particular color of light transmission through the fluid sample disposed in the optical block and wherein the fluid sample is combined with at least a first reagent.

In yet another embodiment, the spectrophotometer measures a level of chlorine in a ship's ballast water.

According to another aspect, a spectrophotometer for use in an explosive atmosphere includes a purged compartment which has disposed within, at least one light source, and at least one detector. A non-purged compartment has disposed within, an optical block having at least one fluid connection port. A first light pipe is optically coupled between the at least one light source and the optical block. A second light pipe is optically coupled between the optical block and the at least one detector. The non-purged compartment is adapted to perform spectrophotometry of a fluid sample disposed within a sample container in the optical block, and the purged compartment is electrically isolated from the non-purged compartment.

In one embodiment, at least one of the first light pipe or the second light pipe include an acrylic plastic.

In another embodiment, at least one of the first light pipe or the second light pipe include a PTC connector to mechanically coupled the at least one of the first light pipe or the second light pipe to the optical block.

In yet another embodiment, the spectrophotometer further includes another light pipe to illuminate the fluid sample in the optical block with a back light for visual observation of a presence and color of the fluid sample.

In yet another embodiment, the spectrophotometer further including another light pipe to illuminate the fluid sample in the optical block with a calibration light to automatically determine a presence of fluid in the optical block.

In yet another embodiment, the at least one light source includes a visible light.

In yet another embodiment, the spectrophotometer includes a colorimeter, and wherein the detector measures an amplitude of light at a particular color.

In yet another embodiment, the detector measures an amplitude of light at a particular color of light transmission through the fluid sample disposed in the optical block and wherein the fluid sample is combined with at least a first reagent.

In yet another embodiment, the spectrophotometer measures a level of chlorine in a ship's ballast water.

According to yet another aspect, a method of measuring a presence or concentration of an organic or inorganic compound in a fluid in an explosive atmosphere includes: providing a spectrophotometer including: a purged compartment having disposed within: at least one light source, at least one detector, a non-purged compartment having disposed within: an optical block having at least one fluid connection port, a first light pipe optically coupled between the at least one light source and the optical block, and a second light pipe optically coupled between the optical block and the at least one detector; purging the purged compartment with a positive air pressure; filling a sample container with the fluid to be tested; injecting at least one reagent into the fluid; measuring an amount transmission of a light from the light source transmitted through the fluid and reagent via the first light pipe and the second light pipe to the detector; and determining the presence or concentration of the organic or inorganic compound in the fluid in the explosive atmosphere based on the amount transmission of the light.

In one embodiment, the step of injecting, includes injecting at least one reagent for a detection of chlorine into the fluid, and the step of determining the presence or concentration includes determining the presence or concentration of chlorine in a ship's ballast water.

In another embodiment, the step of injecting, includes injecting at least one reagent to determine the presence or concentration of a micro-organism into the fluid, and the step of determining the presence or concentration includes determining the presence or concentration of the micro-organism in the fluid.

In yet another embodiment, the step of injecting, includes injecting at least one reagent for to determine the presence or concentration of a heavy metal into the fluid, and the step of determining the presence or concentration includes determining the presence or concentration of the heavy metal in the fluid.

The foregoing and other aspects, features, and advantages of the application will become more apparent from the following description and from the claims.

BRIEF DESCRIPTION OF THE DRAWINGS

The features of the application can be better understood with reference to the drawings described below, and the claims. The drawings are not necessarily to scale, emphasis instead generally being placed upon illustrating the principles described herein. In the drawings, like numerals are used to indicate like parts throughout the various views.

DETAILED DESCRIPTION

Definitions

Figure 1:
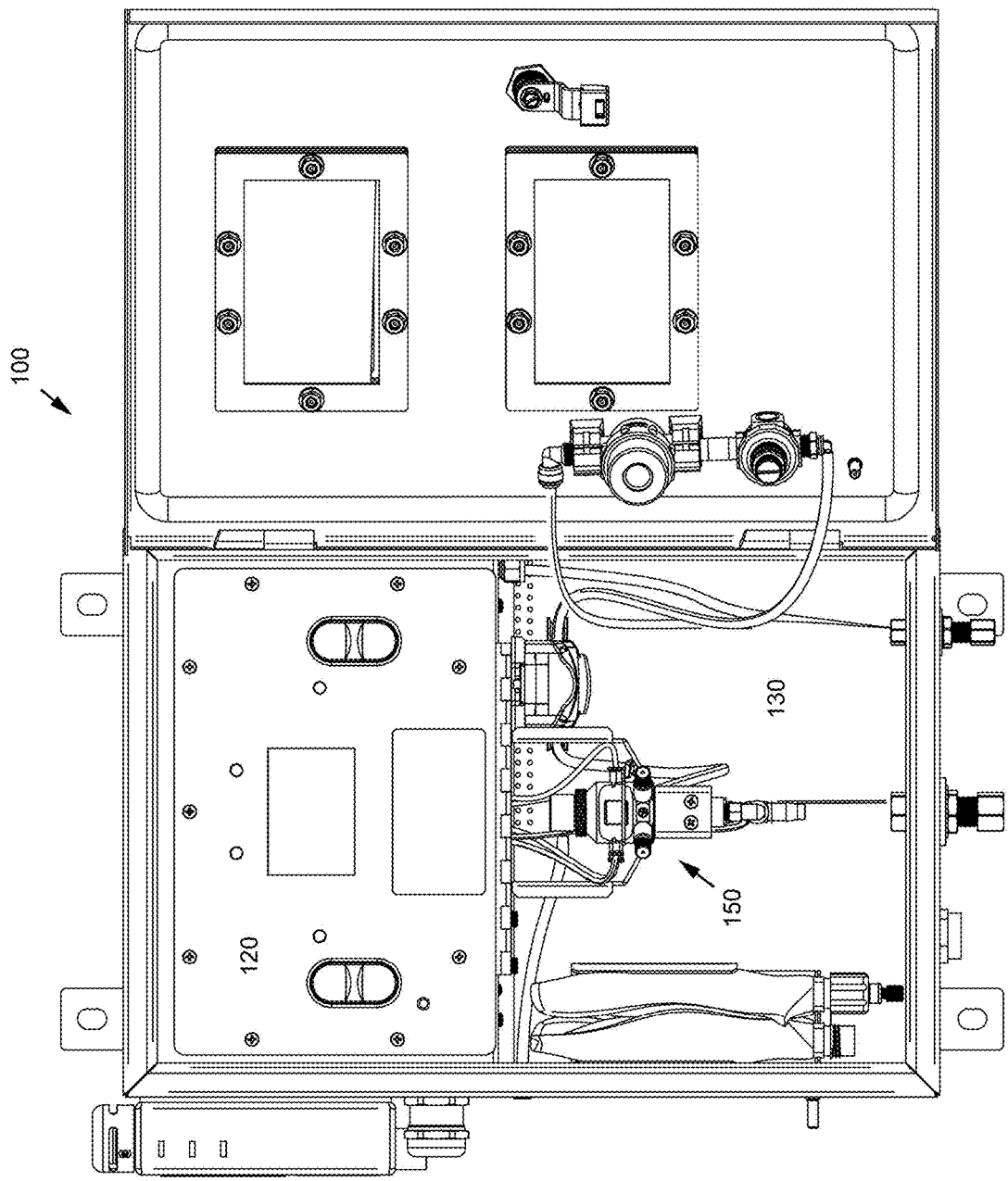
FIG. 1 is a drawing of an exemplary spectrophotometer for use in explosive atmospheres according to the Application.

Light pipe—The light pipe transmits light with a substantially minimal wavelength shift or wavelength distortion of the transmitted light. Light pipes for the spectrophotometer according to the Application are typically formed or cut from an acrylic plastic. As used herein, a light pipe is distinguished from, and does not include typical silica based glass fiber optic cables.

As described hereinabove, a spectrophotometer measures light transmission at a particular wavelength of light through a sample of a fluid. A reagent added to the fluid changes the color of the fluid in response to the presence of certain materials (including certain organic or inorganic materials or substances) in the fluid, thus changing the transmission of light through the fluid based on the presence of a material to be detected. A colorimeter is a type of spectrophotometer operating a visible wavelength. U.S. Pat. No. 8,119,068, FLUID CONTENT MONITOR, assigned to HF Scientific, the same assignee of this Application, describes an exemplary colorimeter as a fluid content monitor including a cuvette, a colorimeter adapted to generate a signal indicative of contents of a fluid sample contained in the cuvette, a container for holding a reagent, and a pump assembly for delivering reagent from the container to the cuvette. The '068 patent is incorporated herein in its entirety for all purposes.

Reagents are available, in development, or contemplated for the detection of a vast variety of organic and inorganic materials, including micro-organisms, metals, alloys, and compounds. These reagents are typically injected into a fluid sample to determine a presence or concentration of the organic and inorganic material in the fluid.

Such fluid testing is common in industrial environments, such as to test the water quality or for particular contaminants in water including waste water, runoff water (e.g. for pesticides), and ballast water (e.g. for chlorine levels in a ship's ballast water).

While spectrophotometers, including colorimeters, are known in the prior art, there is a need for fluid testing in explosive environments, such as, for example in ship ballast tanks, grain production and storage, and mines, etc. To minimize the risk of explosion, fluid to be tested for a certain material content (typically water) must be first removed from the explosive environment before testing.

There is a need for a spectrophotometer which is suitable for use directly in an explosive environment, such as for continuous and automatic monitoring of a fluid directly in the explosive environment.

Another problem is that fluid measuring sensors experience undesired refraction of light transmitted through a fluid where coupled via typical silica based fiber optic cables from a light source to a fluid light transmission sample and to a corresponding detector to measure the transmitted light through the fluid sample. The measurement can be distorted by the light refraction of the fiber optic cables as well as other optical properties of typical silica based fiber optic cables which can cause a shift of wavelength or otherwise introduce a wavelength dependent distortion of the light transmitted for a light source through a fluid sample under test and then to a light detector.

It was realized that a spectrophotometer using light pipes, such as, for example, acrylic plastic light pipes, solved the problems of wavelength distortion imparted by typical fiber optic cables (e.g. single mode and multimode glass fibers). Thus, a spectrophotometer was realized substantially without wavelength distortion that can have separate compartments for electronics components, such as the light source and light detector and for chemistry "wet testing" of a fluid sample under test. Moreover, such light pipes are typically less costly than corresponding lengths of terminated silica based fiber optic cables.

Also, for use in the most dangerous of explosive environments, beyond the electrical isolation imparted by the light pipes, the electronics compartment of the spectrophotometer can be built as a purged compartment. For example, the electronics compartment can be pressurized at a positive air pressure to purge any explosive gas or air suspended particulate matter otherwise present in the explosive atmosphere. Also, with the electrical isolation and physical separation of the fluid sample, an optical mount to perform the wet chemistry (including injection of a reagent into a fluid sample under test) can be present in a non-purged compartment about adjacent to the purged electronics compartment.

FIG. 1 is a drawing of an exemplary spectrophotometer 100 for use in explosive atmospheres according to the Application. The electronics compartment 120 is purged of environmental air by a source of non-explosive pressurized gas. The pressurized gas is typically pressurized air, such as, for example from an air hose connection to an inhouse or shipboard pneumatic air source. Any suitable gas can also be used, such as, for example, any suitable inert gas. The wet chemistry is performed in the non-purged testing compartment 130. While referred to as known in the art as the "wet" or "wet chemistry" side, the testing compartment 130 is substantially dry, and the water or fluid to be tested is pumped into a test container in an optical mount 155. In the exemplary embodiment of FIG. 1, the purged electronics compartment 120 is a second enclosure built into a larger outer industrial enclosure, the part of the outer overall enclosure not contained with the inner box of the electronics compartment 120, being defined as the testing compartment 130. As long as the electronics compartment 120 can be purged of the air from the explosive environment, typically by a positive pressure from a non-explosive air source, it is unimportant how the two compartments are constructed. Where a source of non-explosive pressurized air is available, a cost effective and efficient system and method to pressurize the electronics compartment 120 is by use of a positive pressure non-explosive air source which maintains a pressure within the electronics compartment 120 over the pressure of the surrounding explosive environment, while allowing a slight outflow of the non-explosive pressurized air from the electronics compartment 120 into the surrounding explosive environment.

Beyond removing potentially explosive environmental air from the electronics compartment, removing possible electrical ignition sources from the testing compartment 130 further configures an instrument for permissible use in an explosive environment. Here, flexible light pipes are used to electrically isolate the testing compartment, while transmitting to and receiving light from the optical mount in the testing compartment.

Figure 2A:
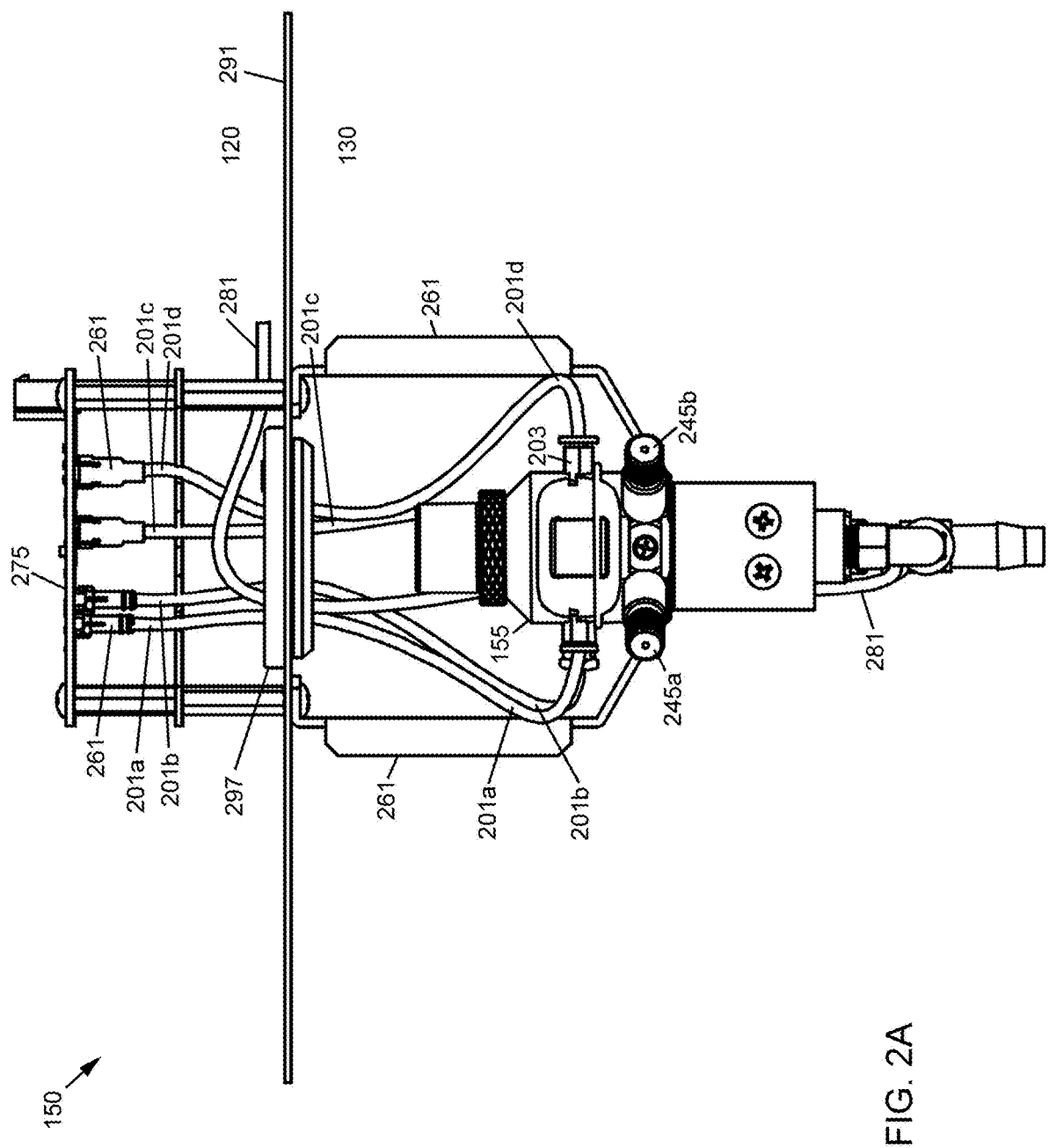
FIG. 2A shows a drawing of an exemplary optical mount assembly and associated fluid, pneumatic, and flexible light pipe connections.

FIG. 2A shows a drawing of an exemplary optical mount assembly 150, and its associated fluid, pneumatic, and flexible light pipe connections. To practice the most basic concept of the new instrument of the Application, a light pipe, here a flexible light pipe 201a, transmits light from a light source in the electronics compartment 120 to the optical mount 155 to illuminate a fluid under test in a transparent or translucent test container in the optical mount 155 in the testing compartment 130. The backlight from back light flexible light pipe 201a is mechanically and optically coupled into the optical mount 155 at termination point 279, FIG. 2B. Another flexible light pipe 201d conveys light transmitted through the sample container (and thus, through the fluid under test) to an optical detector in the electronics compartment 120. While the exemplary instrument uses a light transmission technique, those skilled in the art will understand that any suitable light return to the detector flexible light pipe 201d, such as a reflection test technique, as compared to the exemplary transmission test technique could also be used. In the Exemplary embodiment of FIG. 2A, light pipes are part no. IF 101H-0-17 having a 2.0 mm diameter optical fiber (lightguide), available from Industrial Fiber Optics of Tempe, Ariz. The optical core of the exemplary light pipes is a Super Eska™ with a polyethylene cable jacket. The exact type or circular, square, or rectangular cross section shape and dimensions of any suitable light pipe is unimportant, and any suitable light pipe can be used.

An optional backlight conveyed to the back of the transparent test container (e.g. FIG. 2B, cuvette 277) in the optical mount 155 by a flexible light pipe 201c. The optional backlight illuminates the fluid in the test container so that an observer can see the fluid and the approximate color of the fluid through one or more windows in the spectrophotometer 100 cabinet.

An optional level calibration light provides a light in a physical position on the optical mount 155, such that electronics in the electronics compartment can determine when the fluid test container is full of a fluid under test. While such features can be controlled by hardwired logic, typically the processes of a spectrophotometer 100 (e.g. draining and filling the fluid testing container) are run by one or more microcomputers within the electronics compartment.

The similar looking line 281 is a pneumatic airline used to purge the fluid container before a later sample for test is pumped into the testing container in the optical mount 155.

Exemplary structural brackets 261 are used to mechanically mount the optical head 155 to the bulkhead 291 which defines the break between purged electronics compartment 120 and the non-purged testing compartment 130. Any suitable mounting techniques can be used. Note that feedthrough 297 need not be completely air-tight, because the exemplary positive pressure electronics compartment 120 is not hermetically sealed, but rather allows for a relatively small constant outflow of the non-explosive pressurized air.

On the electronics compartment 120 side, exemplary optical connectors 261 couple each of the flexible light pipes 201a-201c to a light source (typically a light emitting diode (LED)) or to an optical detector (flexible light pipe 201d). On the testing compartment 130 side, it was realized that relatively small threaded push to connect (PTC) style hose fittings 203 (e.g. as can be used for relatively small diameter nylon pneumatic airlines) could be adapted to mechanically couple the flexible light pipes to the optical head 155. In the Exemplary embodiment of FIG. 2A, PTC fittings part no. KQ2H01-32N including an integral release collar, available from the SMC Corp of Noblesville, Ind. were used. Any suitable fitting or connector can be used, such as, for example, any suitable PTC fitting or connector.

The electro-optical components such as LEDs and the detector are typically mounted, such as by soldering, to one or more printed circuit boards (PCB) in the electronics compartment, such as, for example, PCB 275. Flexible light pipes 201a-201d, as well as pneumatic airline 281 can run through the bulkhead 291 by use of any suitable transition, such as for example, a flexible firewall feedthrough 281. Feedthrough 281 need not be air tight, only airflow restricting so as to maintain the positive pressure in the electronics compartment 120.

Figure 2B:
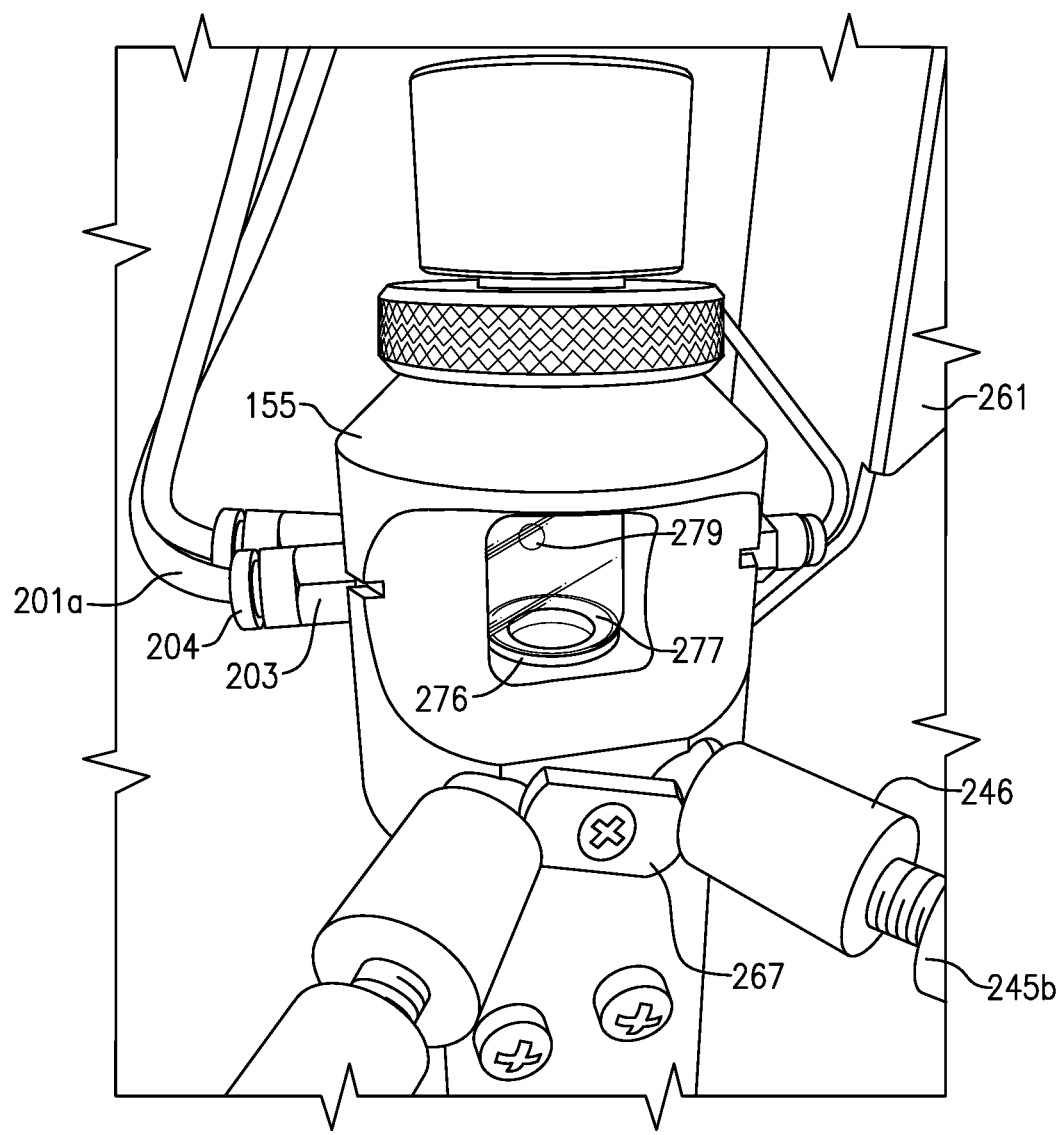
FIG. 2B is a drawing showing a close up view of the optical mount of FIG. 2A.

FIG. 2B is a drawing showing a close up view of the optical mount 155 and its associated connections.

Fluid connectors 245a and 245b couple either or both of two reagent fluids from fluid lines (not shown in FIG. 2A) into the fluid under test in a fluid test container (e.g. FIG. 2B, cuvette 277) in the optical mount 155. Swagelok™ type plastic fluid hose connectors are shown in the exemplary spectrophotometer 100 of FIG. 1, FIG. 2A, and FIG. 2B. Plastic standoffs 246, FIG. 2B, allows Fluid connectors 245a and 245b to thread the Swagelok in one side and injection nozzles into the other side of the plastic standoff 246 which mechanically and fluidly couple to the optical mount 155. In the exemplary embodiment of FIG. 2B, plastic standoffs 246, are secured to respective ports of the optical mount 155 by a double end tapered locking plate 267 affixed to the optical mount 155 by a Philips head screw 268. However, any suitable fluid couplings can be used to couple one or more reagent bags (or any suitable source of reagent) to optical mount 155.

As seen in more detail in FIG. 2B, PTC style hose fittings 203 include inserts 204 and are supplied as such, as one piece. The light pipes (201a-201d) each have an acrylic core which is covered in black rubber or plastic. It was realized that covered light pipe can be robustly mechanically coupled to the various respective ports of the optical mount 155 by use of these PTC connectors otherwise intended for pneumatic or fluid tubes.

In the exemplary embodiment of FIG. 2B, the testing container includes a glass cuvette which is visible through an opening in the optical mount 155. Also, in the exemplary embodiment of FIG. 2B, rubber gasket 276 (e.g. a rubber gasket) is present at both the top and bottom of the cuvette 277. The reticulated part above the cell in this exemplary embodiment is threaded and screws down on to the cuvette compressing the two gaskets to seal the cuvette to the optical mount 155. The cuvette 277 is merely exemplary. Any suitable testing container or sample cell can be used.

Figure 3:
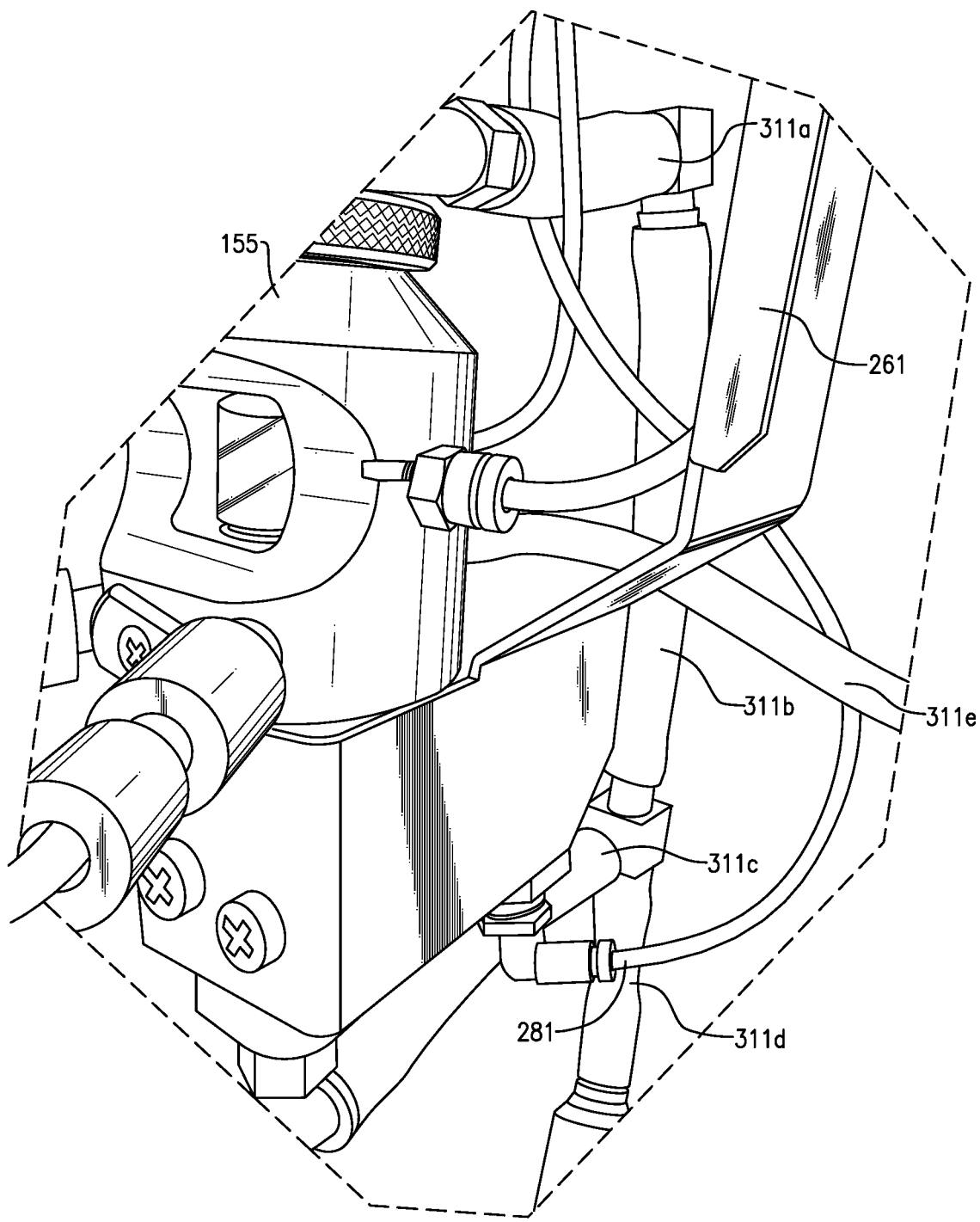
FIG. 3 is a drawing showing an angled side view of the optical mount with associated fluid connections.

FIG. 3 shows an angled side view of optical mount 155 and the associated fluid tubes 311a to 311e which are used to fill, empty, and to flush the sample container within the optical mount 155. Any suitable fluidic arrangement with any suitable filling and flushing process can be used. Fluid tubes 311a to 311e, which operate to perform the wet chemistry flow operations in the non-purged testing compartment 130 of the spectrophotometer 100, are electrically isolated from the electronic circuits of the electronics compartment 120 by light pipes 201a-201d. Note that in the exemplary spectrophotometer 100, electrically conductive components of the optical mount assembly 150, such as metallic optical mount 155, while electrically isolated from the voltages and electrical currents flowing in the electronics compartment 120, are typically electrically grounded to the chassis electrical ground, such as, for example, by metal brackets 261. Any suitable grounding connections, or grounding wires, typically electrically coupled to the metal chassis can be used.

Figure 4:
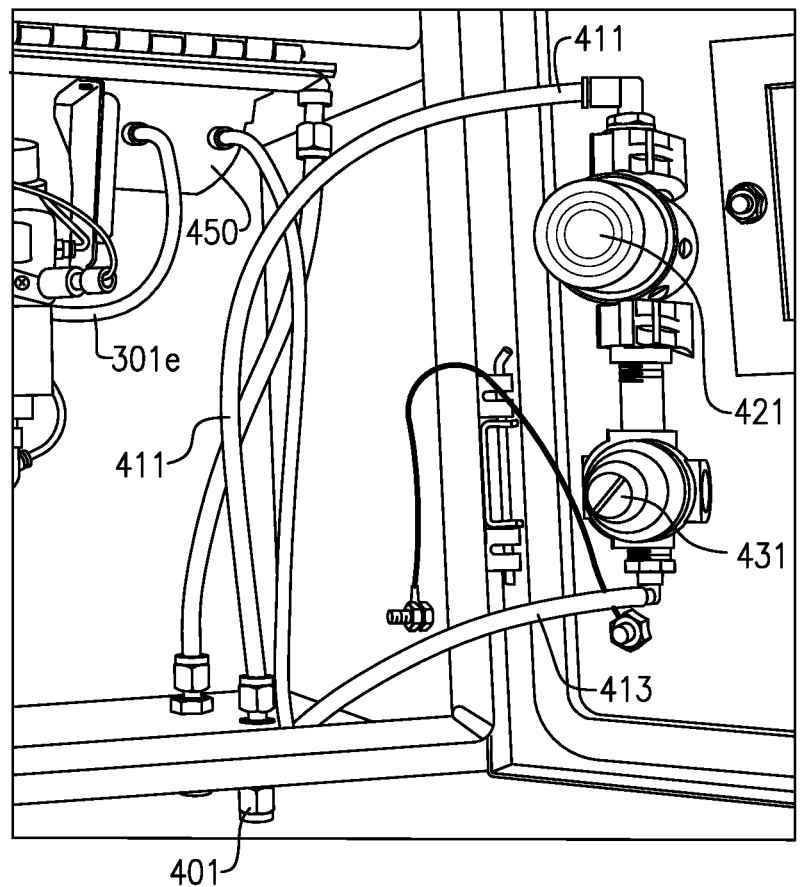
FIG. 4 is a drawing showing fluidic connections of the exemplary spectrophotometer of FIG. 1.

FIG. 4 is a drawing showing fluidic connections of the exemplary spectrophotometer 100 which bring a fluid to be tested into the optical mount 155. Connection 401 is fluidly coupled to a source of fluid to be tested, here configured to test a ballast water of a ship. Tube 411 couples the raw fluid sample to spectrophotometer 100 via a screen assembly 421 and a pressure regulator 431. The screened and pressure regulated fluid is coupled to the optical mount 155 via a motor-controlled valve assembly 450 and tubes 413 and 301e. Any suitable connections to the source of fluid to be tested can be used. Any electrical aspects of the motor-controlled valve assembly 450 are fully contained within the purged electronics compartment 120, with only non-conductive, non-electrical fluid connections and components (of any suitable insulator, such as, for example, plastic or nylon) extending into the non-purged testing compartment 130.

Figure 5:
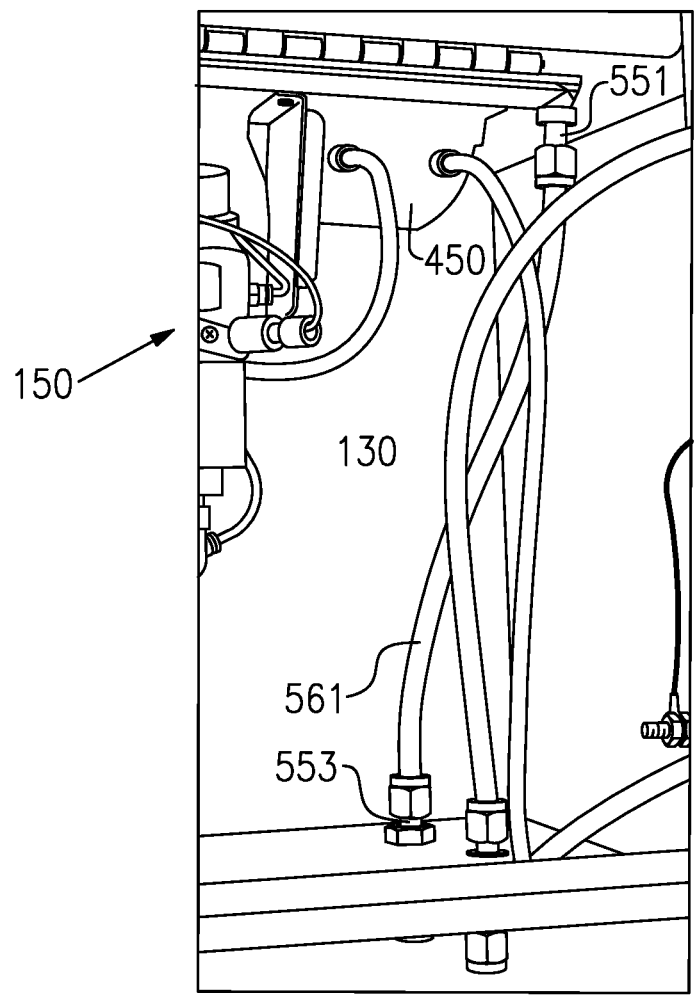
FIG. 5 is a drawing of the testing compartment 130 showing an exemplary pneumatic air connection of the spectrophotometer of FIG. 1.

FIG. 5 is a drawing of the testing compartment 130 showing an exemplary pneumatic air connector 553 which couples pressurized air via nylon tube 561 to another pneumatic air connector 551 which couples the pressurized air into the purged electronics compartment 120. The air routing through the testing compartment 130 is a non-limiting exemplary air run of the exemplary spectrophotometer 100. Any suitable air connection can be made to, and through the cabinet of a spectrophotometer according to the Application. It is not necessary to route the pressurized air through the testing compartment 130. Also, any source of non-explosive air or gas (e.g. a dry nitrogen gas) could be used to purge the electronics compartment 120. For a "pass through" pressurized, but not hermitic purged compartment, there is always an air or gas flow with constant air or gas flow to the environment, therefore use of an available non-explosive air may be more economical than flowing a dedicated gas, such as a dry nitrogen gas.

In FIG. 5, the pressurized or pneumatic air enters the cabinet at bulkhead connector 553, travels via tube 561 to connector 551 at the "firewall" between the non-purged testing compartment 130 and the purged electronics compartment 120 (FIG. 1). This route is unimportant to the invention, however described as the exemplary instrument.

Figure 6:
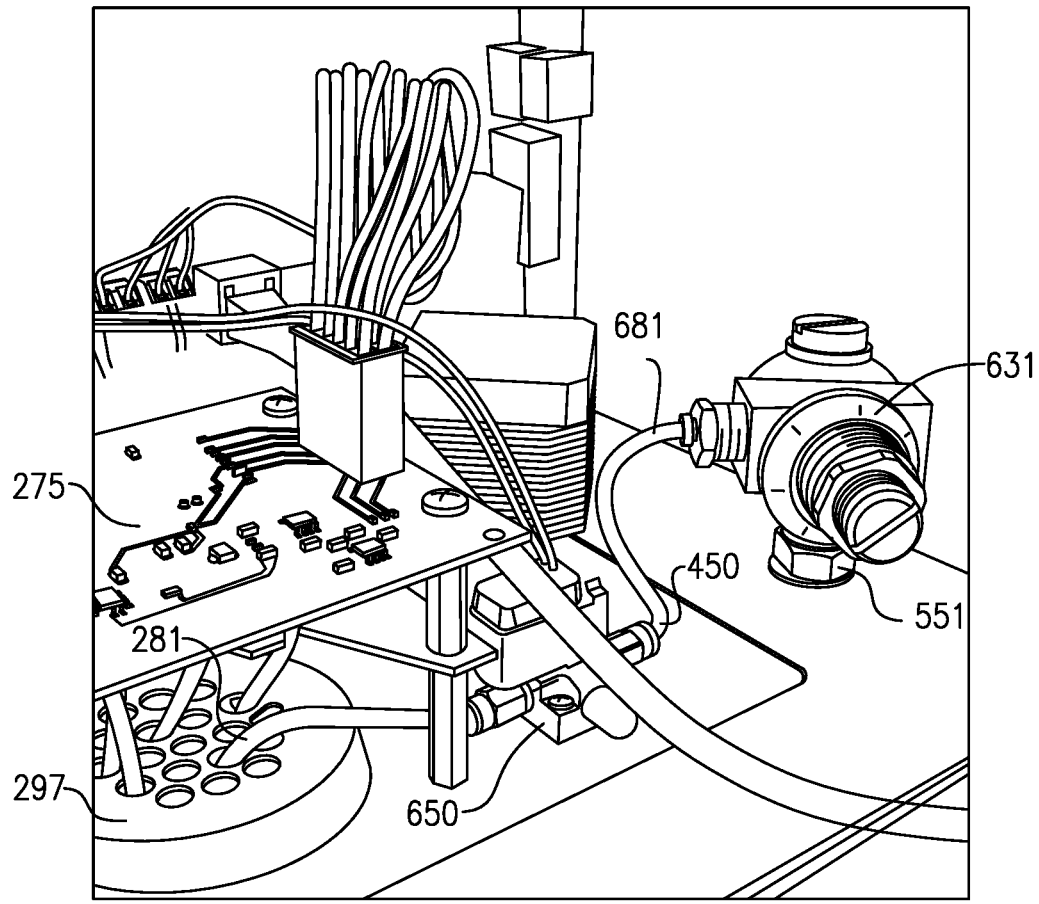
FIG. 6 is a drawing showing internal pneumatic air connections in the electronics compartment of the spectrophotometer of FIG. 1.

FIG. 6 is a drawing showing internal pneumatic air connections in the electronics compartment 130. The pressurized air enters the electronics compartment 130 from the testing compartment 120 below via mechanical air coupler 551. The pressurized air flows into the purged electronics compartment 120 via pressure regulator 631. Pressure regulated air also flows through electrically controlled air valve 650 as part of an air purge process to clear processed sample fluid from the optical mount 155 between sample testing via pressurized air line 281.

Pressure regulator 631 provides a termination point for tube 561. A 3/64" orifice in pressure regulator 631 provides the purge air into the chamber the electronics compartment 130.

In FIG. 6, the outside pressurized air flows as input air to pressure regulator 631. One of the output ports of the pressure regulator 631 flows air through tube 681 to tube 281 via electrically controlled air valve 650, then down through the "firewall" as further detailed by FIG. 2A. Pressurized air also flows through tube 681 to air valve 650 and ultimately down to the drain solenoid used to purge the sample cell, cuvette 277. The drain solenoid (not shown) is programmatically controlled by a microcomputer in the electronics compartment.

Throughout the spectrophotometer, any suitable tube types can be used for pressurized air (e.g. pressurized air to purge the electronics compartment and to flush the sample cell) and for fluid transfer, including reagent flow, and sample fluid flow (e.g. ballast water). Also, any suitable fittings or connectors can be used. The exact or exemplary tube routing is unimportant, such as, for example, it is not necessary to first route the source of pressurized air tube 561 via the testing compartment 130 as sourced by the exemplary NPT feedthrough connector 553 at the bottom wall of the testing compartment 130. Such routing is merely exemplary and illustrative of the exemplary embodiment.

Any firmware or software code, such as for one or more microcomputers operating in the electronics compartment can be proved on a computer readable non-transitory storage medium. A computer readable non-transitory storage medium as non-transitory data storage includes any data stored on any suitable media in a non-fleeting manner Such data storage includes any suitable computer readable non-transitory storage medium, including, but not limited to hard drives, non-volatile RAM, SSD devices, CDs, DVDs, etc.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed is:

1. A spectrophotometer comprising:
an electronics compartment having disposed within:
   at least one light source;
   at least one optical detector;
a testing compartment having disposed within:
   an optical block having at least one fluid connection port;
a first flexible light pipe optically coupled between said at least one light source and said optical block;
a second flexible light pipe optically coupled between said optical block and said at least one optical detector; and
wherein said testing compartment is adapted to perform spectrophotometry of a fluid sample disposed within a sample container in said optical block, wherein said fluid sample is combined with at least a first reagent, and said electronics compartment is electrically isolated from said testing compartment.

2. The spectrophotometer of claim 1, wherein at least one of said first flexible light pipe or said second flexible light pipe comprise an acrylic plastic.

3. The spectrophotometer of claim 1, wherein at least one of said first flexible light pipe or said second flexible light pipe comprise a PTC (push to connect) connector to mechanically coupled said at least one of said flexible light pipe or said second flexible light pipe to said optical block.

4. The spectrophotometer of claim 1, further comprising an additional flexible light pipe to illuminate the fluid sample in said optical block with a back light for visual observation of a presence and color of the fluid sample.

5. The spectrophotometer of claim 1, further comprising an additional flexible light pipe to illuminate the fluid sample in said optical block with a calibration light to automatically determine a presence of fluid in said optical block.

6. The spectrophotometer of claim 1, wherein said at least one light source comprises a visible light.

7. The spectrophotometer of claim 1, wherein said spectrophotometer comprises a colorimeter, and wherein said at least one optical detector measures an amplitude of light at a particular color.

8. The spectrophotometer of claim 1, wherein said at least one optical detector measures an amplitude of light at a particular color of light transmission through the fluid sample disposed in said optical block and wherein said fluid sample is combined with at least a first reagent.

9. The spectrophotometer of claim 8, wherein said spectrophotometer measures a level of chlorine in a ship's ballast water.

10. The spectrophotometer of claim 1, wherein said first flexible light pipe is optically coupled substantially continuously over an entire optical path between said at least one light source and said optical block.

11. A spectrophotometer for use in an explosive atmosphere comprising:
a purged compartment having disposed within:
at least one light source;
at least one detector;
a non-purged compartment having disposed within:
an optical block having at least one fluid connection port;
a first flexible light pipe optically coupled between said at least one light source and said optical block;
a second flexible light pipe optically coupled between said optical block and said at least one detector; and
wherein said non-purged compartment is adapted to perform spectrophotometry of a fluid sample disposed within a sample container in said optical block, wherein said fluid sample is combined with at least a first reagent, and said purged compartment is electrically isolated from said non-purged compartment.

12. The spectrophotometer of claim 11, wherein at least one of said first flexible light pipe or said second flexible light pipe comprise an acrylic plastic.

13. The spectrophotometer of claim 11, wherein at least one of said first flexible light pipe or said second flexible light pipe comprise a PTC (push to connect) connector to mechanically coupled said at least one of said first light pipe or said second flexible light pipe to said optical block.

14. The spectrophotometer of claim 11, further comprising an additional flexible light pipe to illuminate the fluid sample in said optical block with a back light for visual observation of a presence and color of the fluid sample.

15. The spectrophotometer of claim 11, further comprising an additional flexible light pipe to illuminate the fluid sample in said optical block with a calibration light to automatically determine a presence of fluid in said optical block.

16. The spectrophotometer of claim 11, wherein said at least one light source comprises a visible light.

17. The spectrophotometer of claim 11, wherein said spectrophotometer comprises a colorimeter, and wherein said detector measures an amplitude of light at a particular color.

18. The spectrophotometer of claim 11, wherein said detector measures an amplitude of light at a particular color of light transmission through the fluid sample disposed in said optical block and wherein said fluid sample is combined with at least a first reagent.

19. The spectrophotometer of claim 11, wherein said spectrophotometer measures a level of chlorine in a ship's ballast water.

20. A method of measuring a presence or concentration of an organic or inorganic compound in a fluid in an explosive atmosphere comprising:
providing a spectrophotometer comprising: a purged compartment having disposed within: at least one light source, at least one detector, a non-purged compartment having disposed within: an optical block having at least one fluid connection port, a first flexible light pipe optically coupled between said at least one light source and said optical block, and a second flexible light pipe optically coupled between said optical block and said at least one detector;
purging said purged compartment with a positive air pressure;
filling a sample container with the fluid to be tested;
injecting at least one reagent into the fluid;
measuring an amount transmission of a light from said light source transmitted through said fluid and reagent via said first flexible light pipe and said second flexible light pipe to said detector; and
determining the presence or concentration of the organic or inorganic compound in the fluid in the explosive atmosphere based on said amount transmission of the light.

21. The method of claim 20, wherein said step of injecting, comprises injecting at least one reagent for a detection of chlorine into said fluid, and said step of determining the presence or concentration comprises determining the presence or concentration of chlorine in a ship's ballast water.

22. The method of claim 20, wherein said step of injecting, comprises injecting at least one reagent to determine the presence or concentration of a micro-organism into said fluid, and said step of determining the presence or concentration comprises determining the presence or concentration of the micro-organism in the fluid.

23. The method of claim 20, wherein said step of injecting, comprises injecting at least one reagent for to determine the presence or concentration of a heavy metal into said fluid, and said step of determining the presence or concentration comprises determining the presence or concentration of the heavy metal in the fluid.

\* \* \* \* \*